United States Patent [19]

Mathewson et al.

[11] Patent Number: 5,225,161
[45] Date of Patent: Jul. 6, 1993

[54] INTEGRATED MEMBRANE BLOOD OXYGENATOR/HEAT EXCHANGER

[75] Inventors: Wilfred F. Mathewson, Bonsall; Richard L. Bringham, San Clemente; Philip L. Ritger, Huntington Beach; David L. Karshmer, Redwood City, all of Calif.

[73] Assignee: Baxter International Inc., Deerfield, Ill.

[21] Appl. No.: 848,897

[22] Filed: Mar. 10, 1992

Related U.S. Application Data

[63] Continuation of Ser. No. 260,164, Oct. 20, 1988, Pat. No. 5,120,501.

[51] Int. Cl.$^5$ .............................................. A61M 1/14
[52] U.S. Cl. ........................................ 422/46; 422/48; 128/DIG. 3; 261/DIG. 28; 165/141; 165/154; 165/101; 165/179; 165/182; 165/183
[58] Field of Search ............. 422/46, 48; 128/DIG. 3; 261/DIG. 28; 165/141, 154, 101, 177, 179, 182, 183

[56] References Cited

U.S. PATENT DOCUMENTS

| | | | |
|---|---|---|---|
| 3,807,958 | 4/1974 | Brumfield et al. | 128/DIG. 3 X |
| 4,188,360 | 2/1980 | Kurata | 422/46 |
| 4,254,081 | 3/1981 | Streczyn et al. | 422/46 |
| 4,261,951 | 4/1981 | Milev | 422/46 |
| 4,272,373 | 6/1981 | Stenberg et al. | 422/48 X |
| 4,306,018 | 12/1981 | Kirkpatrick | 435/2 |
| 4,376,095 | 3/1983 | Hasegawa | 422/46 |
| 4,424,190 | 1/1984 | Mather et al. | 422/46 |
| 4,612,170 | 9/1986 | Luther et al. | 261/DIG. 28 X |
| 4,639,353 | 1/1987 | Takemura et al. | 422/46 |
| 4,657,743 | 4/1987 | Kanno | 422/46 |
| 4,715,953 | 12/1987 | Leonard | 210/321.8 |
| 4,722,829 | 2/1988 | Giter | 422/46 |
| 4,735,775 | 4/1988 | Leonard et al. | 422/46 |
| 4,791,054 | 12/1988 | Hamada et al. | 435/2 |

FOREIGN PATENT DOCUMENTS

0176651 2/1985 European Pat. Off. .
139562 6/1988 Japan .

*Primary Examiner*—Lynn M. Kummert
*Attorney, Agent, or Firm*—Michael C. Schiffer; Bruce M. Canter

[57] ABSTRACT

A device including an integrally formed membrane oxygenator and heat exchange device positioned in a single housing. The device includes a thermally conductive body formed with a plurality of blood pathways on its surface, and a gas permeable membrane, or membranes positioned in the housing in substantial contact with the heat exchange body to cover or lie within a portion of each of the pathways. The membrane defines a gas pathway separate from the blood pathway through which a gas is directed. The blood is directed through the individual blood pathways. The device also includes various ports and passageways for delivering the blood to the individual channels, and for collecting and removing the blood from the device.

15 Claims, 6 Drawing Sheets

INTEGRATED MEMBRANE BLOOD OXYGENATOR/HEAT EXCHANGER

RELATED CASES

This application is a continuation of co-pending U.S. application Ser. No. 07/260,164, filed on Oct. 20, 1988, now U.S. Pat. No. 5,120,501.

BACKGROUND OF THE INVENTION

The present invention is directed to devices and methods for simultaneously oxygenating, and heating or cooling the blood during surgery. In particular, the present invention is directed to a device which includes an integrally formed heat exchange element and membrane oxygenator.

Devices which heat or cool, and oxygenate the blood are typically used in surgical operations where the supply of blood from the heart is interrupted, e.g. during open heart surgery, or any other surgery performed on the heart or lungs. These devices have been constructed as separate units which are interconnected in an extracorporeal circuit, or have been constructed as a single unit which incorporates the two different devices in separate compartments.

An oxygenation device would be either one of two different types of oxygenators, a bubble oxygenator or a membrane oxygenator. Bubble oxygenators include a gas sparger into which a stream of oxygen bearing gas is directed for forming and dispersing gas bubbles in the blood to perform the oxygenation. Membrane oxygenators direct the blood into contact with a surface or membrane through which gas can diffuse or be transferred. These surfaces or membranes are used to transfer oxygen and carbon dioxide between the blood and an oxygen bearing gas. The benefits and disadvantages of both types of oxygenators are well known and will not be dealt with in any detail herein.

A heat exchange device usually includes a hollow structure, e.g. a coil formed from a thermally conductive material, upon which the blood is directed, while a fluid is passed through the coil. The fluid is either heated or cooled to appropriately heat or cool the coil, and thus the blood.

In recent years the use of membrane oxygenators has increased over the use of bubble oxygenators. This preference of membrane oxygenators over bubble oxygenators has developed because of the damage caused to the blood components when using bubble oxygenators. The precise reasons for this increased use of membrane oxygenators will not be discussed in any greater detail herein.

Commercially available membrane oxygenators include tubing or hollow fibers which are formed from a material through which gas may diffuse under the proper operating conditions. The blood is either passed through the tubing or fibers, with an oxygen bearing gas passed about the fibers, or conversely the blood can be passed about the tubing or fibers with the oxygen bearing gas passed there through. The tubing or the hollow fibers may be formed from silicon, e.g. silicon tubing, or be formed as a porous fiber from a hydrophobic polymeric material.

While some commercially available bubble oxygenators have been provided in a single compartment with a heat exchange device, no commercially available membrane oxygenator has been incorporated with a heat exchange device in a single compartment. That is, the heat exchange device and membrane oxygenator are either provided in separate housings, or the heat exchange and oxygenator are provided in two separate compartments of a single housing. Specifically, the individual compartments may be formed in two separate housings which are joined together to form a single entity, or a single housing is molded with two separate compartments. The blood is transferred between the individual compartments through either tubing, which is connected therebetween, or a manifold which is formed with a fluid passageway connecting one compartment to the other. In either event, both of the compartments will have to be filled with blood in order to adequately perform the heat exchange and the oxygenation.

Examples of various types of units including a heat exchange device and a membrane oxygenator arranged in separate housing compartments joined together to form a single unit are disclosed in U.S. Pat. No. 4,261,951, issued to Milev on Apr. 14, 1981; 4,376,095, issued to Hasegawa on Mar. 8, 1983; 4,424,190, issued to Mather, III et al, on Jan. 3, 1984; and 4,657,743, issued to Kanno on Apr. 14, 1987, and European Patent Application Number 176,651, filed by Mitsubishi Rayon Co. Ltd, on Feb. 14, 1985.

The primary disadvantage with commercially available membrane oxygenators and heat exchange units pertains to the relatively large priming volume of the extracorporeal circuit which includes such devices. Prior to the initiation of surgery the total internal volume of the extracorporeal circuit, which includes the oxygenation and heat exchange devices, as well as other devices must be primed. Priming is performed to flush out any extraneous gas from the extracorporeal circuit prior to the introduction of the blood, and is typically performed with any biocompatible solution, e.g. a saline solution.

The larger the priming volume the greater the amount of priming solution present in the circuit which mixes with the patient's blood. The mixing of the blood and priming solution causes hemodilution, that is the dilution of the blood cells, and in particular the red blood cells for a given volume of fluid. Hemodilution can be disadvantageous since the concentration of blood cells, e.g. red blood cells, must be maintained during the operation in order to minimize adverse effects to the patient. In order to reduce the disadvantage of hemodilution, donor blood, that is blood from other than the patient, is introduced into the diluted blood passing through the extracorporeal circuit. The addition of this blood is performed to raise the blood cell count.

While the addition of this donor blood reduces the disadvantages associated with hemodilution, the donor blood presents other complications, such as compatibility problems between the donor blood and patient's blood, and complications associated with blood borne diseases.

Additional measures taken to correct the effects of hemodilution include the use of hemoconcentrators. Hemoconcentrators are used to concentrate the blood cell count in a given volume of blood. These types of devices are connected in the extracorporeal circuit, and remove a portion of the fluid of the blood which is concentrated by the reduction of fluid. Such devices are expensive and cumbersome to operate.

Thus the increased priming volume created by the use of membrane oxygenators and heat exchange devices in separate compartments or housings presents the disadvantages of hemodilution, and also those disadvantages associated with the correction of the hemodilution.

Another disadvantage with a large priming volume is the amount of time expended in priming the circuit, which increases the start-up time for the surgery. A still further disadvantage with the use of membrane oxygenators and heat exchange devices in separate housings or compartments, is the necessity of connecting such compartments with tubing, or with a manifold passageway. The need to interconnect such compartments or housings with surgical tubing further increases the assembly time of the extracorporeal circuit.

It is thus apparent that it would be advantageous to design a device incorporating a membrane oxygenator and heat exchange device into a single housing compartment. This type of device would reduce the priming volume, and the associated disadvantages with a larger priming volume, and would also reduce the start-up time. Another advantage by combining the heat exchange device and the membrane oxygenator in a single compartment is the reduction in manufacturing cost due to the reduced amount of materials, parts and labor to construct a single housing compartment, instead of two compartments, or two separate housings.

The major impediment in providing the heat exchange device and oxygenator in a single compartment is the requirement of providing sufficient surface area for both heat exchange and for oxygenation. That is, any such combination would have to be able to provide for sufficient surface area to allow for an adequate exchange of heat, and also to perform the desired oxygenation.

A suggested approach to the incorporation of the heat exchange device and the oxygenator in a single compartment is taught in U.S. Pat. No. 4,306,018, issued to Kirkpatrick on Dec. 15, 1981. The gas-heat exchange device illustrated includes a central heat exchange core formed from a thermally transmissive material mounted in a housing. A heat exchange fluid is passed through this core to regulate the surface temperature of the core. The blood is passed through a silicone tube which is wrapped about the exterior surface of the core. The transfer of heat is performed across the core surface and silicone tubing interface. Oxygenation of the blood traveling through the silicone tubing is performed by passing an oxygen bearing gas about the tubing wrapped about the core.

This type of device is disadvantageous because of the inadequacy of the heat transfer, since the heat transfer must occur across the silicone metal interface. Even if the blood is passed outside the silicone tubing, with the gas passed there through, the amount of tubing necessary to effect an adequate gas transfer would require either a substantial wrapping about the core, thus impeding the contact between the blood and the core, or require a relatively large structure to provide for the necessary surface area to obtain adequate heat exchange and oxygenation.

Another device is taught in U.S. Pat. No. 4,715,953, issued to Leonard on Dec. 29, 1987. The device taught in this patent is only described as useful for dialysis, and is not taught, nor intended to perform both gas and heat exchange. The described device includes a plurality of hollow fiber membranes wrapped entirely over the surface of a central core. That is, since the purpose of the device is to provide for an adequate gas exchange the surface of the core is completely covered by the hollow fibers. This eliminates the exposure of the core surface, and thus the ability to use the central core as a heat exchange element. Furthermore, even if the device was modified to pass the blood through the hollow fibers, as is done in the Kirkpatrick patent discussed above, the heat transfer would have to occur across the membrane-metal interface. The resulting device would thus suffer the same disadvantages of the Kirkpatrick device as discussed above.

There thus remains a need to provide a device which would include a membrane oxygenator and heat exchange device as a single integral unit without the disadvantages discussed above.

SUMMARY OF THE INVENTION

The present invention overcomes the above discussed disadvantages by providing a membrane oxygenator and heat exchange device incorporated in a single compartment. This device includes a body formed to define a plurality of pathways through which blood can be passed. Each of the pathways has associated therewith a gas permeable membrane and a heat exchange surface. The device of the invention is operated to simultaneously oxygenate, and heat or cool the blood.

In particular, the blood membrane oxygenator and heat exchange device of the invention includes a thermally conductive structure positioned in a housing, which structure is formed with a plurality of blood receiving channels. Blood passing through each of these channels or passages can be cooled or heated by the appropriate heating or cooling of the thermally conductive structure. The device further includes at least a first gas permeable membrane which is positioned in the housing to define a gas flow pathway, which pathway is separate from the blood receiving channels, and which is formed to be partially received in each of the blood receiving channels.

The device also includes a blood manifold for delivering the blood to the individual blood receiving channels, and a gas manifold which delivers an oxygen bearing gas to the gas flow pathway defined by the gas permeable membrane. The thermally conductive wall is heated or cooled by any suitable means, e.g. by exposure to a heat exchange fluid.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

The present invention is directed to a device which oxygenates, and heats or cools blood during surgical procedures. The reasons for heating or cooling the blood, and for performing the oxygenation, that is typically the exchange of oxygen for carbon dioxide, of a patient's blood during such operations as open heart surgery are well known.

The device of the invention includes a housing which encloses a heat exchange body having an external surface which is formed with a plurality of adjacently located blood receiving channels. The channels define the blood flow pathways of the invention. These blood receiving pathways, as defined by the channels may be integrally formed in the surface of the heat exchange body, e.g. by forming the body's surface with grooves or other types of undulations, or by affixing separately formed channels to the external surface of the heat exchange body. In any event, the individual channels must be in thermal communication with the heat exchange body. In accordance with a preferred embodiment the channels are arranged in a substantially parallel orientation about the external circumference of the heat exchange body.

The device of the invention further includes at least one gas permeable membrane fitted about the heat exchange body to cover, or preferably be partially received in the blood receiving channels. For the purpose of the present invention the term "gas permeable membrane" is meant to include any substrate formed from a material which functions to allow for the transfer or diffusion of gas from one side of the substrate to the other, and in particular, a substrate formed from a material which allows for the transfer or diffusion of oxygen and carbon dioxide gas. Gas permeable membranes suitable for the practice of the invention include, without limitation, porous or non-porous membranes, composite membranes, or symmetric or non-symmetric membranes. Such membranes may be in the form of flat structures, corrugated structures, such as, corrugated sheets, tubular structures, or hollow fibers.

The membrane used in the practice of the invention may be either a single membrane wrapped about the heat exchange surface, or a plurality of individual membranes fitted against the individual channels. The membrane or membranes must also define a gas passageway which is separate from the blood receiving pathway, as defined by the channels. The membrane may be in the form of a sheet or a hollow fiber, both of which types of membranes are well known in the art. The gas passageway may be defined by the internal portion of the membrane, e.g. the interior of porous hollow fiber membranes, or by the positioning of the membrane(s) in the housing to define a gas passageway separate from the blood receiving pathway.

Useful membranes for the device of the invention may be formed from silicone, a polyolefin, e.g. polypropylene or polyethylene, or other suitable hydrophobic polymeric material. The membrane should be formed to have a porosity appropriate for the operational characteristics of the invention. That is, those membranes useful for the practice of the invention allow for the selective diffusion of oxygen and carbon dioxide, while inhibiting the passage of fluids under the operating conditions of the device. These types of membranes will allow oxygen to pass from an oxygen bearing gas to the blood, which is oxygen deficient, while allowing for the transfer of carbon dioxide from the blood to the gas.

As is well known, the rate of gas exchange is dependent upon the permeability of the membrane, as well as the partial pressure of the gases being exchanged within the associated fluid, that is, the oxygen bearing gas and the blood. For a more detailed description of such membranes, and theory of operation, see "Cardiopulmonary Bypass", 2nd Edition, Charles C Reed and Trudi B. Strafford, Texas Medical Press, Inc, 1985, Chapter 28 "Membrane Oxygenator", pages 427–449, which description with respect to such membranes is incorporated herein by reference. The precise type of material from which membranes useful for the invention may be prepared is not critical to the invention, and will not be discussed any further herein.

The preferred membranes are of the type generally known as porous hollow fiber membranes. At least one of these hollow fiber membranes is partially positioned in each of the individual blood receiving channels. In accordance with a more preferable embodiment, a plurality of individual hollow fiber membranes are positioned within each channel. A still further preferred embodiment is where the hollow fibers are woven together using an inert thread. The precise number of hollow fibers is dependent upon the size of the respective channel, the size of the hollow fiber membranes and the desired rate of gas exchange. The types of hollow fiber membranes useful for the practice of the invention are well known, with such membranes described in any one of the above mentioned U.S. patents issued to Mather III et al, Kanno, Hasegawa and Leonard. All such relevant disclosures to such membranes are incorporated herein by reference.

The individual hollow fiber membranes, and individual blood receiving channels form a plurality of individual heat exchange/oxygenation blood flow pathways on the surface of the heat exchange body. Each blood flow pathway is defined by the exposed surface of the individual blood receiving channel, and the external surface of the membranes positioned at the respective channel. The device further includes a mechanism for delivering blood into each of the pathways, so that the blood will flow through the pathway. Blood flowing through the pathway is either heated or cooled, depending upon the requirements of the surgical procedure, and is also subjected to oxygenation.

The precise number of individual channels formed on the external surface of the heat exchange body, and thus the number of blood flow pathways, is dependent upon the desired rate of heat exchange and gas exchange. This is dependent upon the surgical procedure being performed. For certain procedures it is desirable to be able to cool or raise the blood temperature quickly, and as such a greater number of the channels may be needed to accomplish this task. However, this is also a function of the type of materials from which the heat exchange body is formed. A lesser number of channels is needed if the material from which the channels are formed is more thermally conductive. Conversely, if the selected operation does not require the ability to cool or heat the blood quickly then the overall number of channels can be reduced. The same basic principle is also applicable to the rate of gas exchange.

Figure 1:
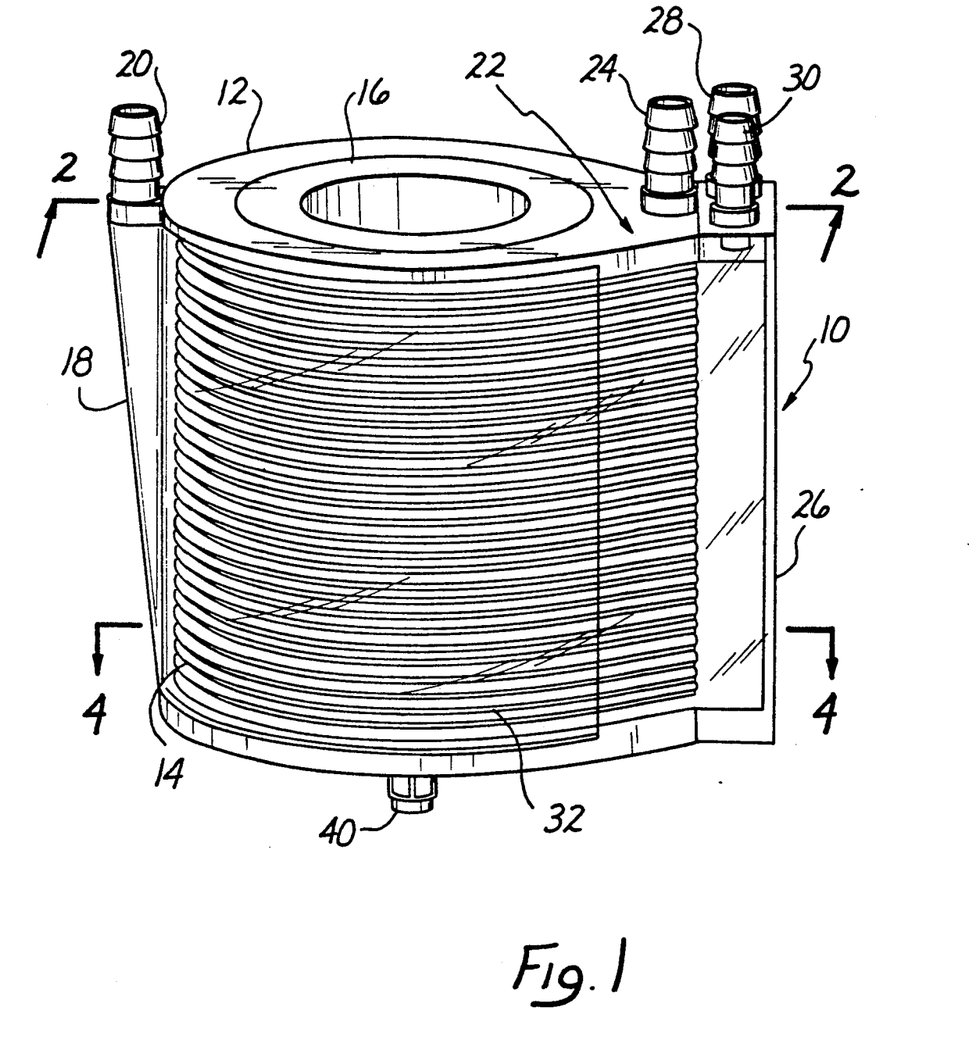
FIG. 1 is a prospective side view of a blood oxygenator/heat exchange device in accordance with an embodiment of the invention.

Referring now to FIG. 1, a specific embodiment of the invention will now be described in greater detail. The heat exchanger/oxygenator device of the invention is seen generally at 10. This device 10 will be connected in an extracorporeal circuit for the purpose of raising or lowering the blood temperature, and performing the necessary gas exchange. The device 10 generally includes an outer housing enclosure 12, in which is mounted a heat exchange body, or bellows 14 and a heat exchange jacket 16.

Figure 2:
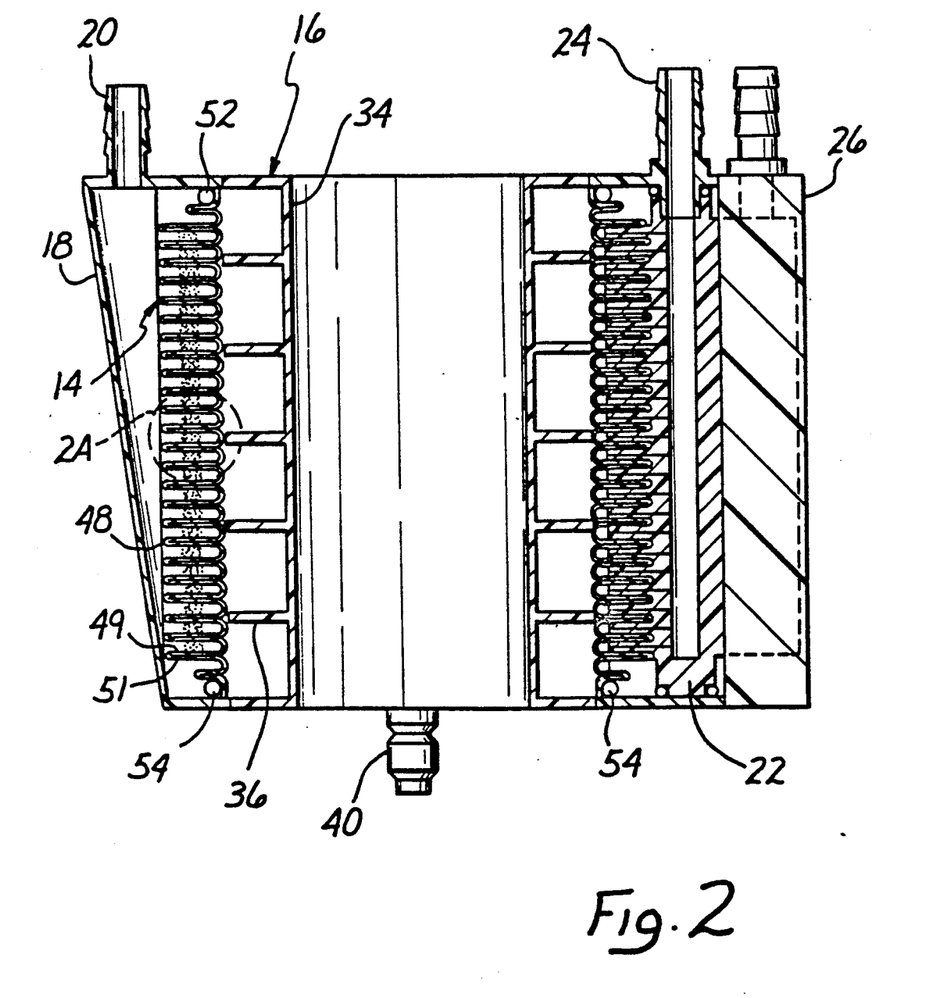
FIG. 2 is a cross-sectional view of FIG. 1 along line 2—2.
Figure 2A:
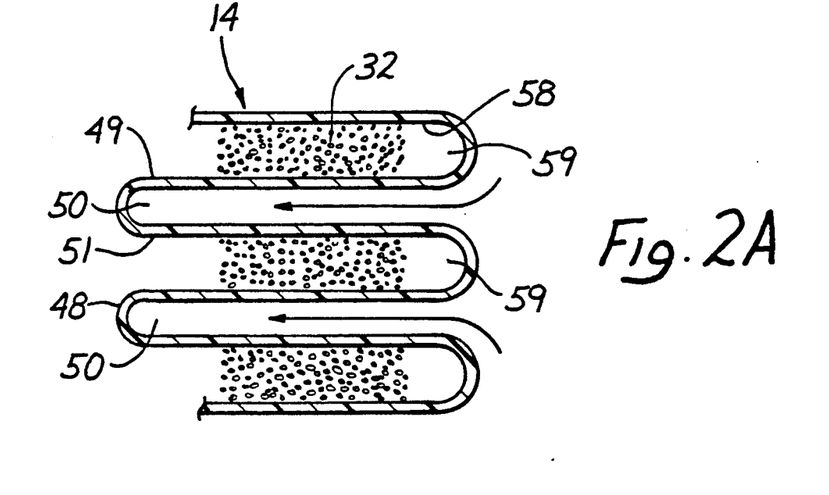
FIG. 2A is an enlarged view of the blood receiving channels, as defined by the pleats of the bellows and the hollow fiber membranes, as seen generally in FIG. 2.

The bellows 14 is formed with a plurality of pleats 48, with a blood receiving channel defined between each of the adjacently positioned pleats 48, such channels best seen in FIG. 2A at 58. The illustrated blood receiving channels 58 are arranged about the circumference of the cylindrically shaped bellows 14 in a substantially parallel orientation. Blood is directed through each of the channels 58 for the purpose of performing the heat exchange and gas exchange. The heat exchange jacket 16, which is positioned within the bellows 14, defines a fluid passage, through which a heat exchange fluid passes to heat or cool the bellows 14. The heat exchange jacket 16 is designed to direct the fluid against the inside surface of the heat exchange body 14, which is formed from a thermally conductive material, i.e. metal. The fluid will thus either heat or cool the body 14, with the blood being directed across the outside surface of the heat exchange body 14 to effect the necessary heat exchange.

The housing enclosure 12 is also formed with a blood exit manifold 18, and exit tubing connector 20. Blood passing through the device 10 will collect in the exit manifold 18 and exit through the tubing connector 20. A tube, not shown, coupled to the tubing connector 20, will direct the blood back to the patient, or to another device in the extracorporeal circuit, not shown. Blood enters the device 10 through a blood manifold, seen generally at 22, which is fitted into the housing enclosure 12. As will be described more fully herein, the blood manifold 22 is formed to deliver blood to the individual blood receiving channels 58. The manifold 22 also includes a blood inlet tubing connector 24 to which a suitable tubing, not shown, is coupled for delivering blood to the device 10 from the patient.

The device 10 further includes a gas manifold 26. This gas manifold 26 may either be a separate structure mounted to the device housing enclosure 12, or integrally formed therewith, and is formed to deliver a gas, typically an oxygen bearing gas, i.e. either pure oxygen or blends of oxygen with other suitable gas, e.g. nitrogen, to the gas passage defined by the gas permeable membrane. As will be discussed more fully herein, in accordance with the preferred embodiment as illustrated in FIGS. 1-4, the gas permeable membrane is formed from a bundle of porous hollow fibers arranged between adjacently positioned pleats of the bellows 14. These fibers, which are generally referenced at 32, are wrapped about the bellows 14, with the opposing open ends of each of the fibers 32 positioned contiguously along the side of the bellows 14, and embedded within a potting polymeric composition, seen at 60. The urethane potting material 60 may be selected from any suitable potting material, e.g. ant of the urethane potting materials taught by the above incorporated references, and in particular the Leonard patent.

As stated, the opposite open ends of the fibers 32 are embedded within the potting material in a side by side relationship. As seen this forms two side-by-side rows of the fiber 32 ends, with such rows seen in FIG. 4 at 31 and 33. The respective individual fiber ends are exposed at a surface of the potting material to provide access into the fibers. Typically, after the fibers have been potted a layer of the potting material, in which the fibers are embedded, is removed to expose the open ends of the individual fibers.

The gas manifold 26 is formed with two side-by-side hollow compartments, as seen at 68 and 70. When the manifold 26 is secured to the device 10, each of these compartments 68 and 70 is arranged over rows 31 and 33 respectively of fiber open ends. The manifold 26 includes ports to allow a gas to be directed into one of these compartments 68 or 70. This gas will then enter the fibers 32 through the open ends, and travel around the bellows 14 through such fibers. The compartment 68 and 70, in combination with the individual fibers 32, define a plurality of separate gas flow pathways around the bellows 14. Furthermore, the individual blood flow pathways are defined by the plurality of individual porous hollow fibers 32 and the individual blood receiving channels 58.

Figure 3:
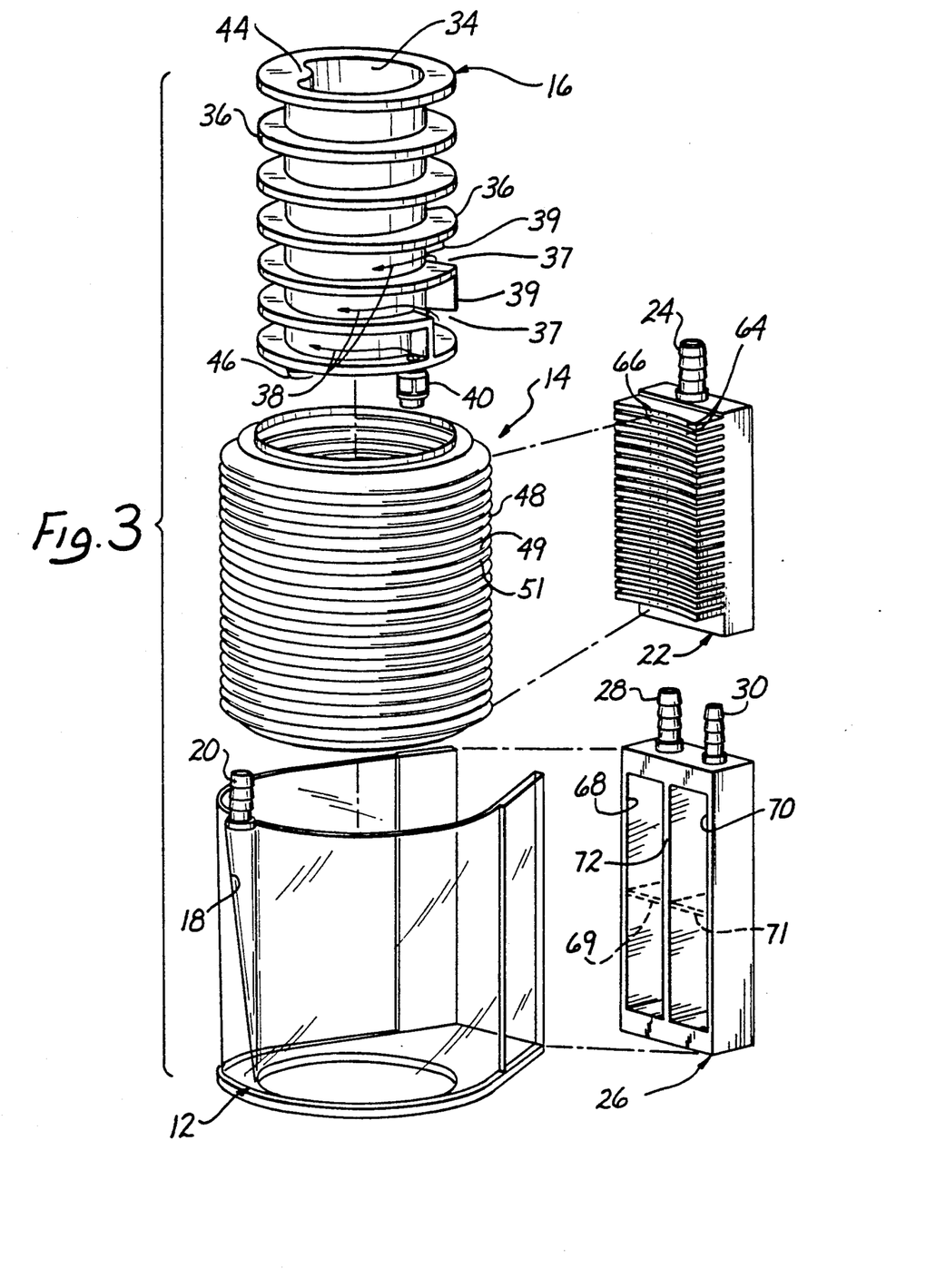
FIG. 3 is an exploded view of the device of FIG. 1.

A more detailed description of the various components of the device 10 will now be discussed with reference to FIGS. 2, 3 and 4. As stated the device 10 is an assembly of the heat exchange jacket 16, nested in the bellows 14, with both being nested in the housing enclosure 12. The cross-sectional diameters of these various components are such to provide a snug fit there between. As seen with particular attention to FIGS. 2 and 3, the heat exchange jacket 16 is a cylindrical body having a substantially smooth cylindrical wall 34. Extending out from this wall 34 are a plurality of ribs, one of which is seen generally at 36. Each rib 36 traverses around the outer circumference of the wall 34 to define individual pathways there between. In order to allow passage of a fluid between adjacently positioned pathways, each rib 36 is formed with an opening, one of which is seen at 37. Adjacent to each of these openings 37 is an upwardly ending extension of the ribs 36, one of which is also seen at 39.

The individual openings 37, and extensions 39 are staggered with respect to those openings 37 and extensions 39 of adjacently positioned ribs 36. This defines a single fluid pathway, which is generally referenced at 38, from one-end to the other and about the outer circumference of the wall 34. The pathway travels from one portion of the pathway 38, as defined between adjacently positioned ribs 36, to another through the openings 37 of the respective ribs 36. This fluid pathway 38 is enclosed by positioning of the jacket 16 inside the bellows 14.

Entrance to the pathway 38 is gained through an inlet tubing connector 40. This connector 40 communicates directly with the pathway 38. The fluid exits the pathway 38, and thus the device 10, through an exit conduit 44, which is formed with an outlet tubing connector 46. The exit conduit 44 is formed along the innermost surface of the wall 34, that is the opposite surface from out of which the individual ribs 36 extend. The conduit 44 is formed with an opening which communicates with the end of the pathway 38, that is that portion defined by the last two ribs 36. This exit conduit 44 runs down the entire length of the wall 34, with the outlet connector 46 formed at the same side of the jacket 16 as the inlet connector 40. It should be noted that the positioning of the outlet connector 46, and inlet connector 40 at the same side of the jacket 16 is merely for convenience of the perfusionist who will typically be connecting the device 10 in the extracorporeal circuit.

As stated the fluid pathway 38 is defined by the positioning of the jacket 16 inside the bellows 14. The bellows 14 is a generally rigid structure formed from a thermally conductive material, typically a metal, e.g. stainless steel. The bellows 14 is formed with numerous pleats 48, with the individual blood receiving channels 58 being defined between adjacently positioned ones of the pleats 48. The precise number of pleats 48 is not critical, and is dependent upon the desired heat exchange and oxygenation characteristics for the particular device 10. This is dependent upon the desired surgical procedure for which the device 10 is to be employed.

Each of the pleats 48 is defined by two walls, seen generally at 49 and 51, which are angularly positioned with respect to each other. The inner surface of the walls 49 and 51 define a space 50, which is positioned along the side of the bellows 14 opposite the channels 58. The space 50 is formed to face the jacket 16 so as to define a portion of the fluid pathway 38. The fluid will travel through this space 50, and thus come into intimate contact with the respective walls 49 and 51. The opposite surfaces of these walls 49 and 51 defines the blood receiving channels 58. The blood passing through the blood receiving channels 58 will thus come into intimate contact with these surfaces of the walls 49 and 51. This arrangement ensures efficient cooling or heating of the blood.

The nested arrangement of the jacket 16, and the bellows 14 are positioned within the housing enclosure 12. As stated, these components are dimensioned to ensure a snug fit. The device 10 is sealed at the junction of these various components by O-rings which are wedged between meeting such components, a first ring seen generally at 52, and a second ring being seen at 54. The housing enclosure 12, bellows 14 and jacket 16 may be secured together by any suitable means, e.g. by being bolted together, or more preferentially by a suitable adhesive.

While the heat exchange fluid pathway 38 is defined by the combination of the jacket 16 nested in the bellows 14, the blood pathway is defined by the blood receiving channels 58, in combination with the gas exchange membrane defined by the fibers 32, with one of the blood pathways 59 best seen in FIG. 2A. As illustrated, the blood pathway 59 is seen as a gap between the fibers 32 positioned between the pleats 48, and the exterior surfaces of the pleat walls 49 and 51. The bundle of fibers 32 will fill a portion of the area defined by the individual blood receiving channel 58, with the precise area filled by the fiber 32 bundle not critical to the invention. However, it has preferentially been found that sufficient oxygenation is obtained when the fiber 32 bundle fills at least forty percent, and preferably greater than sixty percent of the area of the associated channel 58. More preferably the fiber 32 bundle should fill from about forty to about sixty percent of the blood receiving channel 58.

While the illustrated embodiment forms a gap to define the blood pathway 59, the fiber 32 bundles may in fact completely fill the individual channels 58. The resulting device 10 would not have blood pathways 59 as seen in the illustrated embodiment. That is, the pathways 59 would not be defined by a gap, but would merely be a pathway formed about the bellows 14 including the blood receiving channels 58 and the individual fibers 32. The resulting pathway would flow between the pleats 48 defining the respective channel 58, and about the fibers 32.

The above described embodiment of the invention which provides that the hollow fibers completely fill the area defined between the adjacently positioned pleats 48 defining the channel 58, with the blood flowing about the hollow fibers through the pathway 59, has not been found as effective at regulating the temperature of the blood as the embodiment described above in conjunction with FIGS. 1-4. It is believed that by directing the blood into a specifically defined blood pathway 59, that is by defining the pathway 59 as a gap, the optimum degree of temperature exchange is obtained. This is believed to result from the blood directly contacting the thermally conductive surface of the bellows 14 as it travels through the pathway 59 between the channel 58 and fibers 32.

As stated, the gas manifold 26 is formed with two compartments, seen respectively at 68 and 70. The gas manifold 26 is generally rectangular shaped body with the individual compartments separated by a partition wall 72. The gas manifold 26 is mounted to the housing 12 contiguous with the urethane potting material 60. Each of the compartments 68 and 70 is positioned to selectively cover one of the rows 31 or 33 of the exposed fiber open ends. This arrangement defines a gas entrance and exit to the fibers 32, via a respective one of the compartments 68 and 70.

The gas manifold 26 is further formed with a gas inlet port 28 and a gas outlet port 30. These ports 28 and 30 communicate with the compartments 68 and 70, respectively. Gas is delivered into the device 10 by connecting a source of oxygen bearing gas to the gas inlet port 28 which delivers the gas to the compartment 68. The gas enters the compartment 68 entering the individual hollow fibers 32 through each of the exposed fiber open ends. The gas travels about the bellows 14 through the individual hollow fibers 32, and exits into the compartment 70 out from the opposite exposed fiber open ends.

The urethane potting material 60, not only fixes the fibers 32 in position, but also fixes the blood manifold 22 in the housing 12. The blood manifold 22, which is best seen in FIG. 3, is an elongated body formed with a centrally disposed conduit 62 running through its length, as seen in FIG. 4. This conduit 62 is closed at one end and open at the opposite end to the blood inlet tubing connector 24. The manifold 22 is further formed with a plurality of fingers 64 which extend outward from the same side of the manifold 22. These fingers 64 are spatially separated from each other and have a generally rectangular shape. The fingers 64 are also dimensioned to snugly fit between the adjacently disposed pleats 48 of the bellows 14 between the two side-by-side hollow fiber rows 31 and 33. As stated, the manifold is fixed in this position by the urethane potting material 60.

Figure 4:
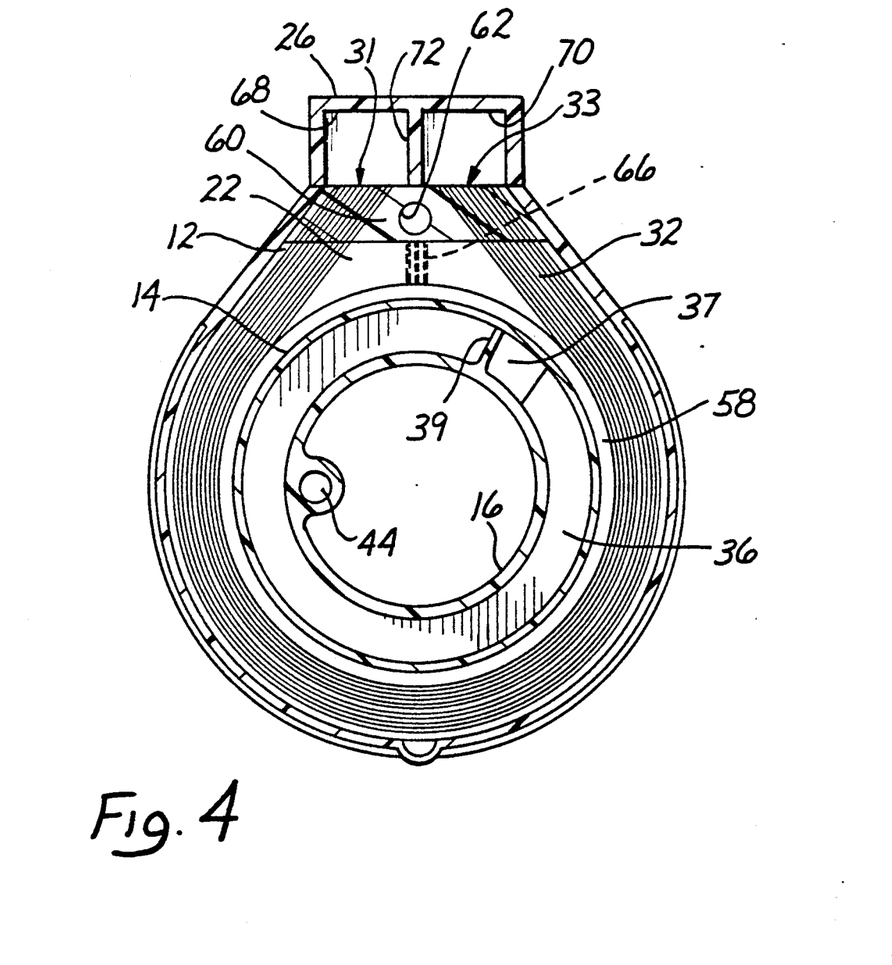
FIG. 4 is a cross-sectional view of FIG. 1 along line 4—4.

As best seen in FIG. 4, each finger 64 is formed with one or more open passages, one of which is seen generally at 66. Each of these passages 66 communicates with the conduit 62, and with the associated blood pathway 59 when the respective finger 64 is fitted between the pleats 48. Blood entering the blood manifold 22 travels through the conduit 62, and selectively enters and flows through each of the passages 66. The blood will exit the passages 66 into the associated blood pathway 59. The blood will then travel through the individual blood pathway 59 about the bellows 14. As the gap defining the blood pathway 59 fills, the blood flows outwards, about the hollow fibers 32 disposed in the associated blood receiving channel 58.

As the blood flows about the individual hollow fibers 32 the exchange of gases occurs. This gas exchange is basically a diffusion process where the oxygen diffuses from the higher concentration in the gas across the fiber membrane to the blood, and the carbon dioxide diffuses from the higher concentration in the blood across the fiber membrane to the gas. The blood will thus become oxygenated as it passes around the individual hollow fibers, and will be subjected to heat exchange by direct contact with the thermally conductive surfaces 49 and 51 of the bellows 14.

The regulation of oxygen and carbon dioxide exchange can be independently controlled by regulating the flow rate of the oxygen bearing gas through the hollow fibers 32, and by regulating the concentration of the oxygen in such gas. This manner of independently controlling the rate of oxygen and carbon dioxide exchange is known. However, it may be desirable to independently control the rate of carbon dioxide and oxygen exchange in a different manner. Accordingly, in accordance with another embodiment, the gas manifold 26 may be formed with each of the compartments 68 and 70 being further sub-divided into two or more separate portions by partition walls, with such walls being shown in phantom in FIG. 3 at 69 and 71. Preferably only that compartment functioning as the gas intake compartment is sub-divided in this manner. That is, only compartment 68 is sub-divided into two separate portions. The remaining compartment 70 remains undivided. By introducing an oxygen bearing gas into only one of the portions of compartment 68, while introducing an inert gas into the other portion, the level of carbon dioxide removal is maintained while the level of oxygen exchange is reduced. This is performed without adjusting the flow rate of the oxygen bearing gas.

This desire to independently adjust the exchange rates for oxygen and carbon dioxide is particularly advantageous when the patient is under hypothermia, that is when the patient's blood temperature has been lowered. In this state the patient's requirement for oxygen diminishes since the patient's metabolism decreases. Thus the oxygenation requirement diminishes. However, the necessity of removing the carbon dioxide remains constant. The described embodiment of the device of the invention would allow for control in the level of oxygenation by merely fluctuating the delivery of the oxygen bearing gas and the inert gas to the individual portions of the compartment 68.

In accordance with still further embodiments of the invention the device 10 is provided with more than one blood manifold, or with more than one gas manifold. In particular, reference is made to FIGS. 5 A-C for schematic illustrations of these embodiments. The embodiment illustrated in FIG. 5C is formed to provide the flow paths for the blood and gas as illustrated for the device 10 described above, which is the preferred embodiment of the invention. In this embodiment the blood has what is termed, a cross-flow in relation to the fiber membranes. That is, the flow path of the illustrated device has a single blood manifold and a single gas manifold, both of which are contiguously arranged at one side of the device. The blood enters the blood pathways, flows about the bellows, and then passes across the diffusion membrane, i.e. in a direction substantially perpendicular to the direction of gas flow through the fibers. It is believed that the preferred embodiment of the invention, that is the device having the cross-flow path as illustrated in FIG. 5C, provides for the most efficient gas exchange. Thus the most preferred embodiment of the invention is that illustrated in the FIGS. 1-4, and described above with the blood and gas flow schematically illustrated for the preferred embodiment in FIG. 5C.

Figures 5A, 5B:
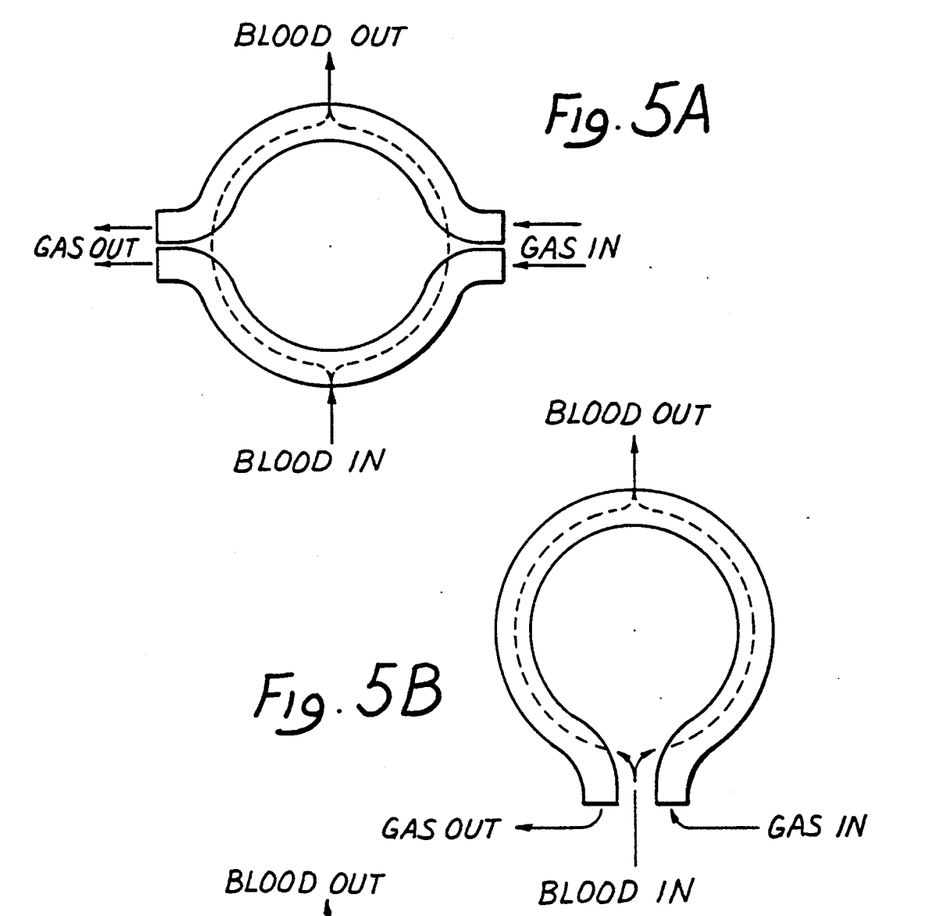
FIGS. 5A-C are schematic illustrations of different embodiments of blood oxygenator/heat exchange devices in accordance with the invention illustrating the blood and gas flow paths through each such embodiments.
Figure 5C:
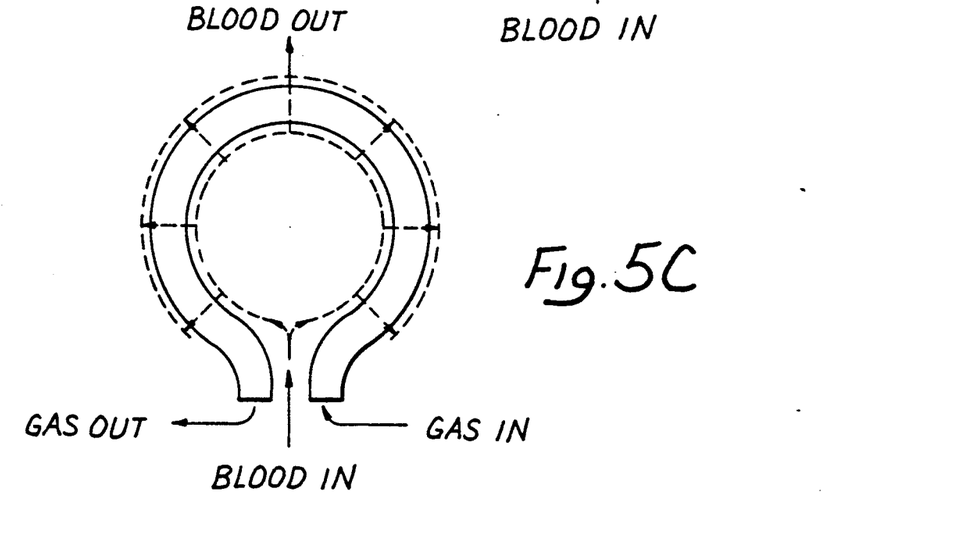

FIG. 5A illustrates a blood flow path for a device incorporating two separate gas manifolds, with each gas manifold 26 being as described above for gas manifold 26. This device has the two separate gas manifolds positioned at opposite sides of the device. Two fiber bundles would be arranged in each of the blood pathways, as defined by a blood receiving channel, with the opposite ends of each fiber embedded in a potting material to expose the fibers 32 open ends. Individual gas manifolds would be mounted to the device to cover the exposed open ends in a manner similar to the manner in which the manifold 26 was mounted in the device 10 as described above. These manifolds would have separate compartments for selectively communicating with respective rows of open fiber ends to define two separate gas flow pathways in each of the blood pathways. The oxygen bearing gas can be delivered to both compartments of one gas manifold, with the other manifold functioning as an exit manifold for the spent gas, that is the gas passing out of the fibers after oxygenation.

The device illustrated in FIG. 5B would include two separate blood manifolds. In this embodiment the second blood manifold would communicate directly with the blood pathway, as does the blood manifold 22 described above. In this embodiment the blood would not pass through the fiber bundles, but will flow through each of the blood pathways and exit the pathway through the second blood manifold. While this embodiment may increase the flow rate of the blood through the device, it is believed that the extent of oxygenation would be lower in this embodiment than with the preferred embodiment. As stated, it is theorized that since this embodiment does not require the blood to pass about the individual hollow fiber membranes to exit the device, the blood would not be exposed to the same total surface area of the fiber membranes as provided with the preferred embodiment described and illustrated in FIGS. 1-4.

The overall configuration of the device could be modified to provide still further embodiments of the present invention. For example, the device may include a plurality of individual thermally conductive tubes into which a plurality of hollow fiber membranes are positioned. These tubes, with the fibers in place, would be held in a housing which includes the necessary conduits and ports for delivering an oxygen bearing gas through the individual hollow fiber membranes, and for directing blood through the individual thermally conductive tubes. A fluid exchange medium, i.e. water, would be passed about the exterior of the individual thermally conductive tubes.

Figures 6, 7, 8:
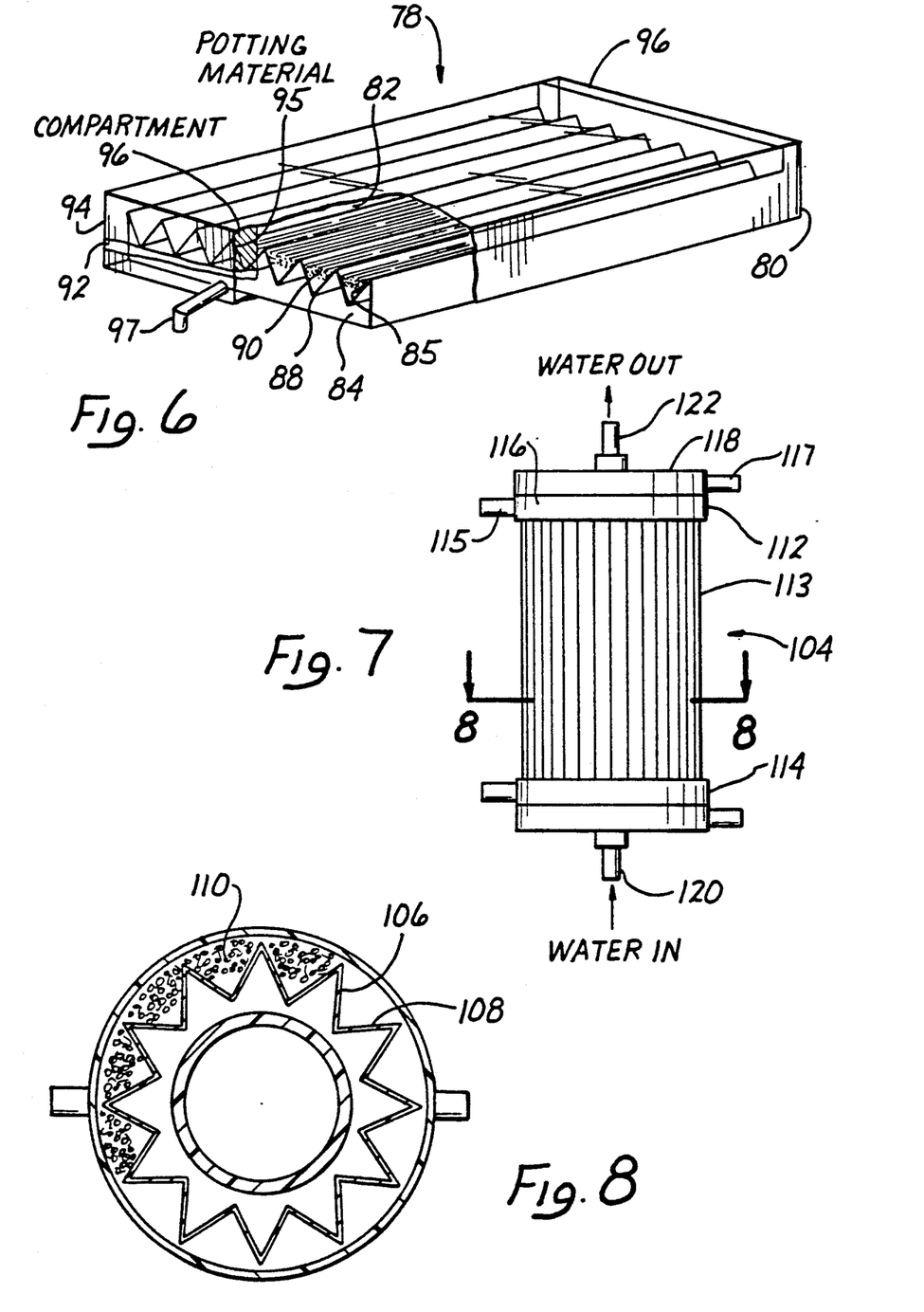
FIG. 6 is a partially sectioned prospective view of a blood oxygenator/heat exchange device in accordance with another embodiment of the invention.
FIG. 7 is a side view of a blood oxygenator/heat exchange device in accordance with a further embodiment of the invention.
FIG. 8 is a cross-sectional view of FIG. 7 along line 8—8.

Another embodiment would substitute the cylindrical bellows 14 for a relatively flat device. This embodiment is illustrated in FIG. 6. A device 78 includes a generally rectangular housing 80 divided into two distinct internal chambers 82 and 84, by a pleated partition wall 88. The area between adjacent pleats defines individual blood receiving channels 85, with a single or a bundle of hollow fibers, or for that matter any other suitable gas exchange membrane, positioned in the blood receiving channels in a manner similar to as described above, with such fibers generally seen at 90. In the illustrated embodiment the fibers in combination with the channels, as defined between the pleats of the partition wall 88, define the blood pathway.

A blood manifold is fitted at each side of the device housing, with one such manifold seen at 92. Each blood manifold is formed with fingers, not shown, similar to the fingers 64 described above. These fingers fit into the blood receiving channels 85 for delivering or receiving blood therefrom. In this regard, manifold 92 will function as the inlet manifold, while the other manifold will function as the blood outlet. The device 78 also includes two gas manifolds positioned at opposite sides of the device 78 in a position contiguous to the blood manifolds. These gas manifolds, one of which is seen at 94, are positioned above the associated blood manifold 92 and are formed with a compartment 96 which communicates with the open ends of the fibers positioned in the blood receiving channels. As with the above described embodiment, the opposite ends of the individual fibers are embedded in a potting material to expose their open ends. The potting material is seen generally at 95. A heat exchange jacket is formed by the chamber 84, with a heat exchange fluid, not shown, merely directed through this chamber 84 via conduit 97.

A still further embodiment is seen generally in FIGS. 7 and 8. In accordance with this illustrated embodiment a device 104 includes a cylindrically shaped heat exchange body with the blood pathways defined longitudinally along the exterior surface. This embodiment is similar in design as the embodiment illustrated in FIGS. 1-4, except that the blood pathways are arranged lengthwise, instead of about the circumference of the bellows. The remaining components of the device are appropriately configured to deliver the blood and oxygen bearing gas to the blood and gas pathways.

The device, seen at 104 includes a housing 113 in which is mounted a bellows 106. Bellows 106 has individual pleats 108 running lengthwise, instead of about the circumference of the bellows 14 described above for the preferred embodiment. The individual hollow fibers, or other suitable membrane, as seen generally at 110, are positioned in the area defined between the adjacently positioned pleats 108, which define a blood receiving channel. The respective end of the fibers 110 are potted in a urethane material, not shown, to expose the open end in a manner similar to that described above.

The device includes any suitable arrangement of manifolds for delivering the gas and blood to the respective blood and gas pathways. As illustrated the device 104 includes a single combined gas and blood manifold fitted to the housing 113 opposite ends, with such manifolds seen at 112 and 114 respectively. The manifold 112, which can serve as the intake manifold, includes two portions, seen at 116 and 118 respectively. The portion 116 includes channels, not shown, positioned contiguous to the exposed open ends of the hollow fibers. A gas is introduced into the channels of the portion 116 through a gas inlet port 115. The gas enters and flows through this portion 116, entering the respective exposed open ends of the individual hollow fibers. The manifold portion 118 includes channels, not shown, which communicate with the blood receiving channels, as defined between the adjacently positioned pleats 108. The manifold 112 includes one or more blood inlet ports, one of which is seen at 117 which communicates with the channels of the portion 118. The portion 118 may also be formed with individual fingers, not shown, which extend out therefrom into the individual blood receiving channels as do the fingers 64 described above. Each of these fingers would include one or more passages which communicates and directs the blood to the associated blood receiving channel. The opposing manifold 114 would be formed similar to the manifold 112 for receiving the blood and gas passing out of the blood channels and fibers 110.

Finally, the device 104 includes inlet and outlet ports for a heat exchange fluid, with the inlet seen at 120 and the outlet seen at 122. The fluid is directed into a fluid pathway formed inside the bellows 106.

While the preferred embodiments have been described and illustrated, various modifications and substitutions may be made thereto without departing from the scope of the invention. Accordingly, it is to be understood that the invention has been described by way of illustration and not limitation.

What is claimed is:

1. A blood oxygenator and heat exchange device comprising a body means for defining a plurality of pathways through which blood can be passed, with each of said pathways having disposed therein multiple gas permeable membranes and defined at least partially by a pair of heat exchange surfaces, each of said pathways being between said pair of heat exchange surfaces.

2. The device of claim 1 wherein said multiple gas permeable membranes are substantially contiguous to said pair of heat exchange surfaces so that said multiple gas permeable membranes and said pair of heat exchange surfaces are in intimate contact with blood flowing through said pathways.

3. A blood oxygenator and heat exchange device comprising:
   a housing formed to allow blood to pass there through; and
   heat and gas exchange means positioned in said housing for selectively exchanging heat and gas with blood passing through said housing, said exchange means at least partially forming a plurality of blood flow pathways, each pathway being formed between at least a pair of thermally conductive walls and having at least a first gas permeable membrane.

4. The device of claim 3 wherein each of said pathways includes a plurality of gas permeable membranes, with each of said membranes being spatially separated from adjacently positioned membranes to allow for the flow of blood there between.

5. The device of claim 3 wherein each of said pathways includes a plurality of porous hollow tubular gas exchange membranes, with the internal portion of each of said porous hollow tubular membranes defining a passage through which may be directed an oxygen bearing gas.

6. The device of claim 5 wherein each of said porous hollow tubular membranes are spatially separated from adjacent tubular membranes to allow for the flow of blood there between.

7. The device of claim 3 wherein each of said at least a pair of thermally conductive walls is formed to define a channel through which blood can pass, with each of said gas permeable membranes being positioned between said at least a pair of thermally conductive walls in a respective one of said defined channels, and at least partially filling said respective channel.

8. A blood oxygenator and heat exchange device comprising:
    housing;
    a thermally conductive heat exchange body disposed within said housing;
    said thermally conductive body having an external surface formed to define a plurality of blood receiving channels;
    blood ports formed in said housing for selectively distributing blood through each said blood receiving channels;
    heat exchange means for selective heating or cooling of said thermally conductive heat exchange body, said plurality of blood receiving channels and the blood flowing therethrough;
    at least a first gas permeable membrane which is positioned in said housing to define a gas flow pathway and which is formed to be partially received in each of said blood receiving channels; and
    gas ports formed in said housing for directing a gas through said gas flow pathway.

9. The device of claim 8 wherein said heat exchange means is an internal chamber formed in said thermally conductive body for receiving a heat exchange fluid for selective cooling or heating of said thermally conductive body.

10. The device of claim 9 wherein said at least a first gas permeable membrane is a plurality of individual gas permeable membranes selectively positioned in each of said blood receiving channels.

11. The device of claim 10 wherein said individual gas permeable membranes are a plurality of porous hollow fibers positioned in each of said blood receiving channels.

12. The device of claim 11 wherein said plurality of hollow fibers positioned in each of said blood receiving channels are spatially separated from each other to allow for the flow of blood there between.

13. A device of claim 10 wherein said individual gas permeable membranes are porous hollow fibers.

14. The device of claim 8 wherein said heat exchange means is positioned in said thermally conductive body and is constructed and arranged operable for heating or cooling said body.

15. A blood oxygenator and heat exchange device comprising:
    a housing;
    a thermally conductive body positioned in said housing to subdivide said housing into first and second separate chambers, said thermally conductive body having a first surface facing into said second chamber which is formed with a plurality of blood receiving channels;
    blood delivery and receiving ports formed in said housing for delivering and receiving blood from said plurality of blood receiving channels;
    heat exchange means positioned in said housing first chamber, said heat exchange means being constructed and arranged for heating or cooling said thermally conductive body, said plurality of blood receiving channels and the blood flowing therethrough;
    at least a first gas permeable membrane means positioned in said second chamber and partially within each of said blood receiving channels, said at least a first membrane means and said second chamber defining a gas passageway separated from said plurality of blood receiving channels by said at least a first membrane means; and
    a gas delivery port formed in said housing for directing a gas into said second chamber.

* * * * *